(12) United States Patent
Iwama (10) Patent No.: US 12,035,967 B2
(45) Date of Patent: Jul. 16, 2024

(54) BEAM PROFILE CONVERTER, CATHETER DEVICE, AND LASER ABLATION DEVICE

(71) Applicant: FURUKAWA ELECTRIC CO., LTD., Tokyo (JP)

(72) Inventor: Masaki Iwama, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 313 days.

(21) Appl. No.: 16/951,403

(22) Filed: Nov. 18, 2020

(65) Prior Publication Data

US 2021/0085395 A1 Mar. 25, 2021

Related U.S. Application Data

(63) Continuation of application No. PCT/JP2019/022883, filed on Jun. 10, 2019.

(30) Foreign Application Priority Data

Jun. 13, 2018 (JP) .................................. 2018-112560

(51) Int. Cl.
*A61B 18/24* (2006.01)
*A61B 18/00* (2006.01)
(Continued)

(52) U.S. Cl.
CPC .............. *A61B 18/24* (2013.01); *G02B 6/262* (2013.01); *G02B 27/0927* (2013.01);
(Continued)

(58) Field of Classification Search
CPC .......... A61B 18/24; A61B 2018/00577; A61B 2018/2211; A61B 2018/2244;
(Continued)

(56) References Cited

U.S. PATENT DOCUMENTS 5,077,815 A 12/1991 Yoshizawa et al.
5,290,280 A 3/1994 Daikuzono
(Continued)

FOREIGN PATENT DOCUMENTS

CN 1049977 A 3/1991
CN 102778729 A 11/2012
(Continued)

OTHER PUBLICATIONS

J. W. Kim, J. I. Mackenzie, J. R. Hayes, and W. A. Clarkson, "High-power Er:YAG laser with quasi-top-hat output beam," Opt. Lett. 37, 1463-1465 (2012) (Year: 2012).*
(Continued)

*Primary Examiner* — Joseph M Dietrich
*Assistant Examiner* — Ranjani Mari Sundaresan
(74) *Attorney, Agent, or Firm* — Oblon, McClelland, Maier & Neustadt, L.L.P.

(57) ABSTRACT

For the purpose of efficiently converting a beam profile of laser light with a simple configuration, provided is a beam profile converter including: a first optical fiber that outputs guided light from a first end surface; and a second optical fiber being a multi-mode optical fiber to which the light is input to a second end surface and configured to guide the light, in which a core diameter of the second optical fiber is larger than a core diameter of the first optical fiber at the first end surface, and the light output from the first end surface is input to a core portion of the second end surface at a position separated from an optical axis of the second optical fiber in a direction inclined with respect to the second end surface.

10 Claims, 10 Drawing Sheets

(51) Int. Cl.
  *A61B 18/22* (2006.01)
  *G02B 6/26* (2006.01)
  *G02B 6/32* (2006.01)
  *G02B 6/34* (2006.01)
  *G02B 27/09* (2006.01)

(52) U.S. Cl.
  CPC .............. *A61B 2018/00577* (2013.01); *A61B 2018/2211* (2013.01); *A61B 2018/2244* (2013.01); *A61B 2018/2272* (2013.01); *G02B 6/32* (2013.01); *G02B 6/34* (2013.01)

(58) Field of Classification Search
  CPC .... A61B 2018/2272; A61B 2018/2035; A61B 2018/20554; G02B 6/262; G02B 27/0927; G02B 6/32; G02B 6/34; H01S 3/10; H01S 3/00
  See application file for complete search history.

(56) References Cited

U.S. PATENT DOCUMENTS

| | | | |
|---|---|---|---|
| 5,953,477 A | * | 9/1999 | Wach .................. G02B 6/4203 385/115 |
| 7,916,386 B2 | | 3/2011 | DiGiovanni et al. |
| 2007/0237449 A1 | | 10/2007 | Aoki et al. |
| 2008/0180787 A1 | | 7/2008 | DiGiovanni et al. |
| 2014/0003456 A1 | | 1/2014 | Mikliaev et al. |
| 2015/0293306 A1 | | 10/2015 | Huber et al. |
| 2017/0299900 A1 | | 10/2017 | Montoya et al. |
| 2017/0351029 A1 | | 12/2017 | Morasse et al. |
| 2020/0209478 A1 | | 7/2020 | Fujita |

FOREIGN PATENT DOCUMENTS

| | | | | |
|---|---|---|---|---|
| CN | 103149638 | A | | 6/2013 |
| EP | 1 950 852 | A2 | | 7/2008 |
| JP | 2-93408 | A | | 4/1990 |
| JP | 2-93612 | A | | 4/1990 |
| JP | H0293612 | A | * | 4/1990 |
| JP | 3-94744 | A | | 4/1991 |
| JP | 2000-47065 | A | | 2/2000 |
| JP | 2008-187176 | A | | 8/2008 |
| JP | 2012-43820 | A | | 3/2012 |
| JP | 2014-503856 | A | | 2/2014 |
| JP | 2015-188900 | A | | 11/2015 |
| JP | 2017-51985 | A | | 3/2017 |
| JP | 2017-173371 | A | | 9/2017 |
| JP | 2017-535810 | A | | 11/2017 |
| WO | WO 2017/212711 | A1 | | 12/2017 |
| WO | WO 2018/042715 | A1 | | 3/2018 |

OTHER PUBLICATIONS

International Search Report issued Aug. 20, 2019 in PCT/JP2019/022883 filed Jun. 10, 2019, 2 pages.
Combined Chinese Office Action and Search Report issued May 27, 2022 in Patent Application No. 201980038556.0 (with English language translation and English translation of Category of Cited Documents), 20 pages.
Extended European Search Report issued Feb. 4, 2022 in corresponding European Patent Application No. 19818919.3, 13 pages.
Chinese Office Action issued Jan. 20, 2023 in Chinese Patent Application No. 201980038556.0 (with unedited computer-generated English Translation), 17 pages.
Office Action issued Nov. 22, 2022, in corresponding Japanese Patent Application No. 2020-525545 (with English Translation), 9 pages.

* cited by examiner

BEAM PROFILE CONVERTER, CATHETER DEVICE, AND LASER ABLATION DEVICE

CROSS-REFERENCE TO RELATED APPLICATION(S)

This application is a continuation of International Application No. PCT/JP2019/022883, filed on Jun. 10, 2019, which claims the benefit of priority of the prior Japanese Patent Application No. 2018-112560, filed on Jun. 13, 2018, the entire contents of which are incorporated herein by reference.

BACKGROUND

The present disclosure relates to a beam profile converter, a catheter device, and a laser ablation device. There is known a technique of inserting a catheter to which an optical fiber is inserted, into a patient's body to perform treatment. Such a technique is used with a laser ablation device, for example. The laser ablation device is used by inserting a catheter into the body of a patient, outputting laser light for ablation from the tip of an optical fiber to be applied to a target site such as an affected part for treatment. The laser ablation device is sometimes used to irradiate the epidermis of the patient with laser light.

It is sometimes more preferable that the beam profile of the laser light for ablation has a top hat shape rather than a Gaussian shape having a sharp peak. Compared with a case where the beam profile has the Gaussian shape, the laser light with a beam profile of a top hat shape can uniformly apply light energy to a wider area without giving excessive light energy to the target site in a depth direction, for example. Various techniques of converting the beam profile of laser light into a top hat shape have been disclosed (see, for example, Japanese Unexamined Patent Application Publication Nos. 2017-535810 and 2014-503856, and Japanese Laid-open Patent Publication Nos. 2017-051985, 2015-188900, and 2017-173371). Converting the beam profile in this manner is also referred to as homogenization.

However, the techniques in Japanese Unexamined Patent Application Publication Nos. 2017-535810 and 2014-503856, and Japanese Laid-open Patent Publication Nos. 2017-051985 and 2015-188900, use a special optical fiber for converting to a top hat shape or require an additional special optical element, and thus do not have simple configurations. Furthermore, the technique in Japanese Laid-open Patent Publication No. 2017-173371 is a technique of inclining the optical axis of the laser light to be input to the optical axis of the optical fiber for conversion to the top hat shape, in which the conversion of the beam profile is not always efficient and thus needs a certain optical fiber length in order to achieve sufficient conversion.

SUMMARY

There is a need for providing a beam profile converter, a catheter device, and a laser ablation device capable of efficiently converting a beam profile of laser light with a simple configuration.

According to an embodiment, a beam profile converter includes: a first optical fiber that outputs guided light from a first end surface; and a second optical fiber being a multi-mode optical fiber to which the light is input to a second end surface and configured to guide the light. Further, a core diameter of the second optical fiber is larger than a core diameter of the first optical fiber on the first end surface, and the light output from the first end surface is input to a core portion of the second end surface at a position separated from an optical axis of the second optical fiber in a direction inclined with respect to the second end surface.

DETAILED DESCRIPTION

Hereinafter, embodiments of the present disclosure will be described in detail with reference to the accompanying drawings. The present disclosure is not limited to the embodiments described below. Furthermore, the same or corresponding elements are appropriately assigned the same reference numerals in the description of the drawings. Moreover, the drawings are schematic, and the dimensional relationship between individual elements, the ratio of individual elements, or the like might differ from actual situation. Furthermore, the individual drawings might include portions having mutually different dimensional relationships and ratios. In addition, the directions will be illustrated with reference to the xyz coordinate axes, which are appropriately illustrated in the figures.

First Embodiment

Figure 1:
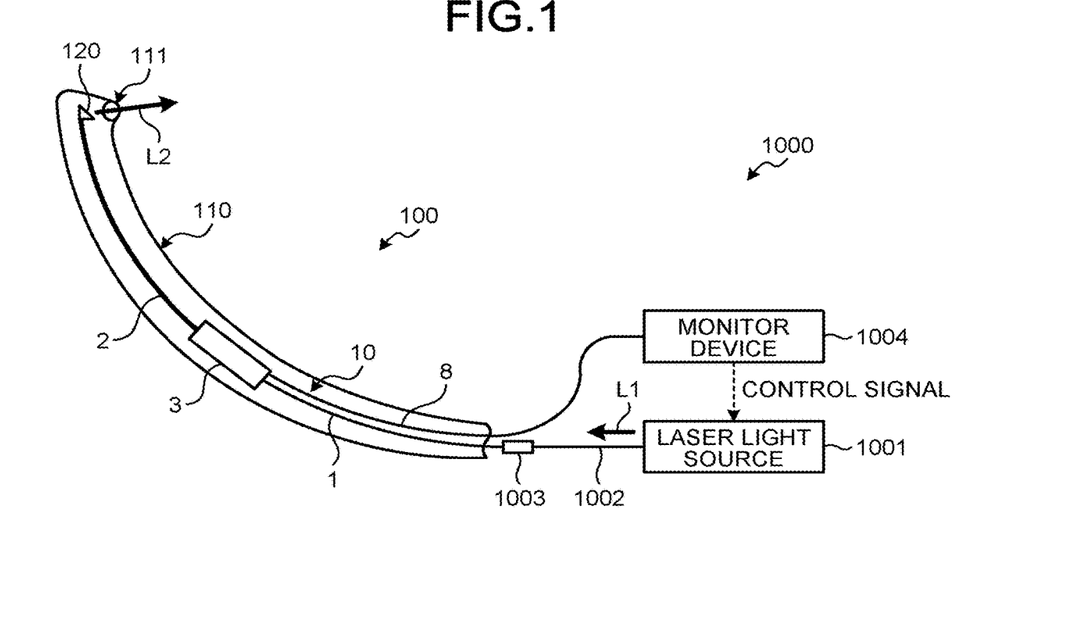
FIG. 1 is a schematic diagram illustrating a schematic configuration of a laser ablation device according to a first embodiment.

FIG. 1 is a schematic diagram illustrating a schematic configuration of a laser ablation device according to a first embodiment. A laser ablation device 1000 includes a laser light source 1001, an output optical fiber 1002, a connecting portion 1003, a monitor device 1004, and a catheter device 100. The catheter device 100 includes a catheter body 110, an optical element 120, and a beam profile converter 10. The beam profile converter 10 includes at least an optical fiber 1, an optical fiber 2, and a housing 3.

The laser light source 1001 includes a laser light source such as an optical fiber laser and outputs laser light L1 for ablation to the output optical fiber 1002. The output optical fiber 1002 is a single-mode optical fiber or a multi-mode optical fiber. The output optical fiber 1002 is optically connected to the optical fiber 1 of the beam profile converter 10 via the connecting portion 1003. With this configuration, the laser light source 1001 can output the laser light L1 to the optical fiber 1.

The catheter body 110 in the catheter device 100 is formed of a flexible material such as resin. The catheter body 110 may have a laser light output window 111 formed of a material having excellent laser light transmission properties. For illustrative purposes, the catheter body 110 in FIG. 1 is presented as a transparent illustration. A part of the optical fiber 1, the optical fiber 2, and the housing 3, which are at least a part of the beam profile converter 10, are inserted into a lumen of the catheter body 110. The optical element 120 is arranged in the vicinity of the laser light output window 111 in the lumen of the catheter body 110 and is optically connected to the optical fiber 2 of the beam profile converter 10.

Figure 2:
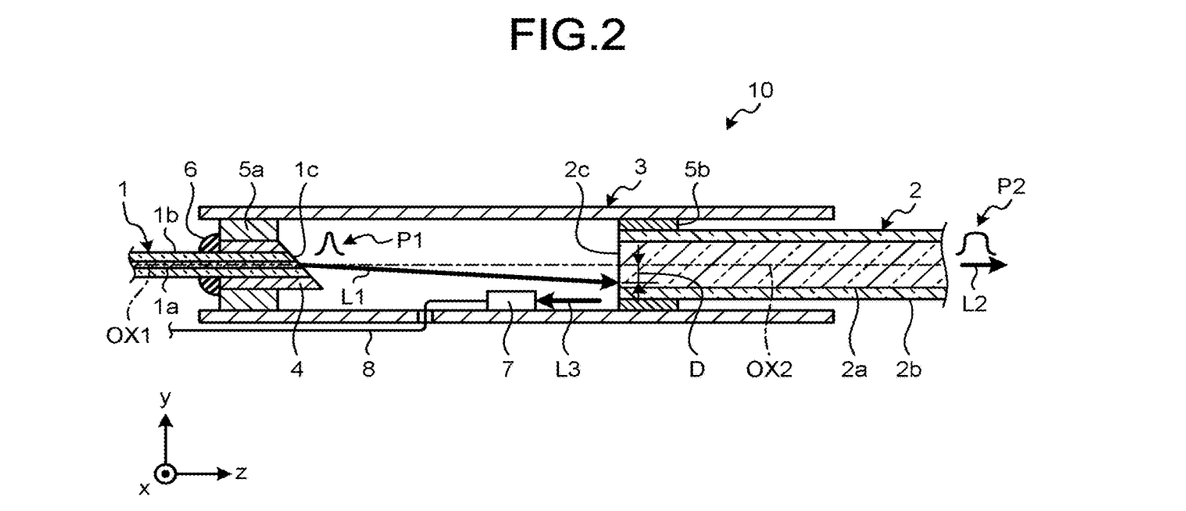
FIG. 2 is a schematic diagram illustrating a schematic configuration of main portions of a beam profile converter.

FIG. 2 is a schematic diagram illustrating a schematic configuration of main portions of the beam profile converter 10. The beam profile converter 10 includes a ferrule 4, fiber fixing members 5a and 5b, a resin 6, a light receiving element 7, and an electric wire 8, in addition to the optical fiber 1, the optical fiber 2, and the housing 3.

The optical fiber 1, which is a first optical fiber, is a single-mode or multi-mode optical fiber including a core portion 1a and a cladding portion 1b. The optical fiber 1 is a step index type or a graded index type multi-mode optical fiber, for example, but is not particularly limited. The optical fiber 1 has a core diameter of 105 μm, a cladding diameter of 125 μm, and a numerical aperture (NA) of 0.15, for example, but is not particularly limited.

The optical fiber 1 has an end surface 1c as a first end surface. The end surface 1c is parallel to the x axis and is inclined with respect to an optical axis OX1 of the optical fiber 1, which is the central axis of the core portion 1a and extends in the z-direction. That is, the optical fiber 1 is cut obliquely. The optical fiber 1 outputs the guided laser light L1 from the end surface 1c. The optical fiber 2, which is a second optical fiber, is a multi-mode optical fiber including a core portion 2a and a cladding portion 2b. The optical fiber 2 is a step index type or a graded index type multi-mode optical fiber, for example, but is not particularly limited. The core diameter of the optical fiber 2 is larger than the core diameter of the optical fiber 1 on the end surface 1c, for example, by 1.5 times or more. The optical fiber 2 has a core diameter of 400 μm, a cladding diameter of 440 and an NA of 0.22, for example, but is not particularly limited.

The optical fiber 2 has an end surface 2c as a second end surface. In the first embodiment, the end surface 2c is orthogonal to an optical axis OX2 of the optical fiber 2 which is the central axis of the core portion 2a and extends in the z direction, and is parallel to the xy plane. The core portion 2a may be exposed on the end surface 2c, or may have a lens, a transparent film or the like being further provided on the end surface 2c. Furthermore, the end surface 2c is not limited to a flat shape, and may be a non-planar shape such as a protruding shape or a recessed shape. In the optical fiber 2, the laser light L1 output from the end surface 1c of the optical fiber 1 is input to the core portion 2a of the end surface 2c, and the laser light L1 is guided along the optical fiber 2. The guided laser light L1 is output to the optical element 120 as laser light L2. The optical element 120 collects the laser light L2, bends its optical path, and outputs the laser light L2 from the laser light output window 111 of the catheter body 110.

Here, using a cladding diameter $\Phi_1$ at the end surface 1c of the optical fiber 1 and a core diameter $\Phi_2$ at the end surface 2c of the optical fiber 2, a distance D between an input position of the light output from the end surface 1c to the end surface 2c of the optical fiber 2 and the optical axis OX2 of the optical fiber 2 is preferably expressed by the following Formula (1).

$$(\Phi_2 - \Phi_1)/2 > D \geq \Phi_1/2 \quad (1)$$

Specifically, when the cladding diameter $\Phi_1$ at the end surface 1c of the optical fiber 1 is 125 μm and the core diameter $\Phi_2$ of the optical fiber 2 is 400 μm, Formula (1) is calculated as: $(400-125)/2 = 135.5 > D \geq 125/2 = 62.5$. Accordingly, the distance D from the optical axis is preferably 62.5 μm or more and 135.5 μm or less.

The housing 3 is a cylindrical body, for example, and accommodates an end including the end surface 1c of the optical fiber 1 and an end including the end surface 2c of the optical fiber 2. Furthermore, the housing 3 has a function of blocking, absorbing and preventing external leakage of stray light, which is a component of the laser light L1 that is not coupled to the core portion 2a of the optical fiber 2. The housing 3 is preferably formed of a material having a high thermal conductivity such as aluminum in order to efficiently dissipate the heat generated by the absorbed stray light.

The ferrule 4 is a cylindrical body formed of zirconia, for example, to which the optical fiber 1 is inserted and fixed, and is obliquely cut at one end side so as to be flush with the end surface 1c. The fiber fixing member 5a is a cylindrical body formed of metal, for example, and fixes the optical fiber 1 to the housing 3 via the ferrule 4. The resin 6 bonds the ferrule 4 and the fiber fixing member 5a. The fiber fixing member 5b is a cylindrical body formed of metal, for example, and fixes the optical fiber 2 to the housing 3. In the state where the optical fiber 1 and the optical fiber 2 are fixed to the housing 3, the relative positional relationship between the optical fiber 1 and the optical fiber 2 is fixed. In the first embodiment, the optical axis OX1 of the optical fiber 1 and the optical axis OX2 of the optical fiber 2 are aligned with each other.

The light receiving element 7 is formed with a photodiode, for example, so as to receive stray light L3 that is a part of the stray light described above and outputs a current signal corresponding to the intensity of the received light to the electric wire 8. The electric wire 8 is connected to the monitor device 1004 as illustrated in FIG. 1. The monitor device 1004 has a function of receiving a current signal and monitoring the intensity of the laser light L1 based on the current signal. Furthermore, the monitor device 1004 has a function of outputting a predetermined control signal to the laser light source 1001 based on the intensity of the monitored laser light L1.

Figure 3:
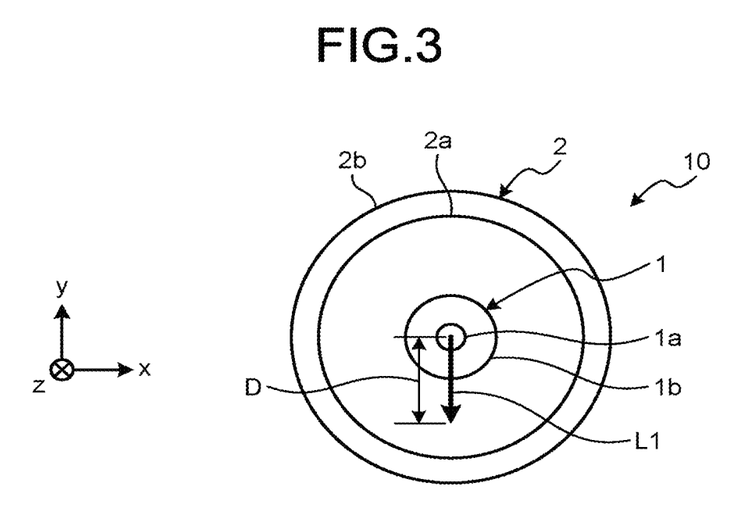
FIG. 3 is a view illustrating an input/output state of laser light.

Next, functions of the beam profile converter 10 will be described in detail with reference to FIGS. 2 and 3. FIG. 3 is a view illustrating an input/output state of laser light, an illustration of the optical fibers 1 and 2 of FIG. 2 viewed in the negative direction of the z axis. The optical fiber 1 outputs the guided laser light L1 input from the laser light source 1001, from the end surface 1c. The end surface 1c is inclined with respect to the optical axis OX1. As a result, due to the refractive index difference between the core portion 1a and the space inside the housing 3, the laser light L1 output from the end surface 1c travels in a direction inclined from the optical axis OX1 within a plane parallel to the yz plane. Note that a beam profile P1 of the laser light L1 is assumed to have a Gaussian shape.

The end surface 1c and the end surface 2c are non-parallel to each other and are separated by an appropriate distance (for example, 100 μm or less on the optical axis). The core diameter of the optical fiber 2 is larger than the core diameter of the end surface 1c of the optical fiber 1. As a result, the laser light L1 output from the end surface 1c is input with low loss to the core portion 2a of the end surface 2c. When input, the laser light L1 is input in a direction inclined with respect to the end surface 2c at a position separated from the optical axis OX2 of the optical fiber 2 by a distance D. In this case, the laser light L1 output from the end surface 1c is inclined with respect to the optical axis OX2 of the optical fiber 2 immediately before and immediately after being input to the core portion 2a of the end surface 2c at a position separated from the optical axis OX2 of the optical fiber 2.

While the optical fiber 2 being a multi-mode optical fiber guides the laser light L1, a Gaussian-shaped beam profile component guided as a meridional ray and a donut-shaped beam profile component guided as a skew ray are generated from the laser light L1. As a result, laser light L2 output from the optical fiber 2 becomes laser light having a top hat-shaped beam profile P2, in which the meridional ray and the skew ray are mixed. That is, the optical fiber 2 functions as an optical fiber that converts the beam profile.

At this time, the laser light L1 output from the end surface 1c is input to the core portion 2a of the end surface 2c in a direction inclined with respect to the end surface 2c at a position (offset position) separated from the optical axis OX2 of the optical fiber 2. This allows the skew rays to be further generated with a relatively short waveguide distance. This results in achievement of efficient beam profile conversion in the optical fiber 2. Furthermore, this makes it possible to reduce the use length of the optical fiber 2 which is relatively expensive due to its large diameter or large NA, realizing an efficient beam profile converter 10 at low cost. In addition, the beam profile converter 10 uses no special optical fiber or an additional special optical element, so as to be implemented with a simple configuration. Furthermore, preferably, when the core diameter of the optical fiber 2 is 1.5 times or more larger than the core diameter of the end surface 1c of the optical fiber 1, it would be possible to perform beam profile conversion with the optical fiber 2 with lower loss and shorter length.

Furthermore, by applying such a beam profile converter 10 having a simple configuration, low cost, and efficiency to the catheter device 100 typically discarded after each use, it is possible to realize the catheter device 100 with low cost.

In this beam profile converter 10, the optical axis OX1 and the optical axis OX2 are aligned to each other, and the end surface 1c and the end surface 2c are made non-parallel, so as to achieve an input state in which the laser light L1 is input in a direction inclined with respect to the end surface 2c at a position separated from the optical axis OX2. However, the configuration of the beam profile converter 10 can be modified to realize the above-described input state. For example, the optical axis OX1 and the optical axis OX2 do not have to be aligned with each other, or the optical axis OX1 and the optical axis OX2 may be non-parallel.

Furthermore, by appropriately adjusting an inclination angle of the end surface 1c with respect to the optical axis OX1, adjusting the distance between the end surface 1c and the end surface 2c, and the combination of the core diameter and the refractive index of the core portion 1a and the core diameter and the refractive index of the core portion 2a, it would be possible to adjust the ratio between the meridional ray component and the skew ray component, leading to adjustment of the beam profile of the laser light L2. For example, it is possible to have a top hat shape close to a Gaussian shape or a top hat shape close to a donut shape. The top hat shape is assumed to have a profile similar to or substantially similar to the super Gaussian shape having an order m of 3 or more. Field U of Super Gaussian is expressed by the following Formula.

Note that ω0 is a spot radius and r is a distance from the center.

$$U = \exp[-(r/\omega 0)^m]$$

Next, effects of the beam profile converter 10 will be described using results of simulation calculation.

Characteristics of the optical fiber 1 are set such that the core diameter is 105 μm, the cladding diameter is 125 μm, the refractive index of the core portion 1a is 1.56, the refractive index of the cladding portion 1b is 1.53, the inclination angle of the normal line with respect to the optical axis OX1 of the end surface 1c is 8°, and the divergence angle of the laser light L1 is 7°. Characteristics of the optical fiber 2 are set such that the core diameter is 400 μm, the cladding diameter is 440 μm, the refractive index of the core portion 2a is 1.56, the refractive index of the cladding portion 2b is 1.53, and the length is 1 m. Subsequently, the positional relationship between the optical axes OX1 and OX2 parallel to each other is adjusted so that the distance D, which is an offset amount from the optical axis OX2, becomes 0 mm, 0.05 mm, or 0.125 mm, and the beam profile of the laser light L2 output from the optical fiber 2 is calculated by simulation.

Figure 4A:
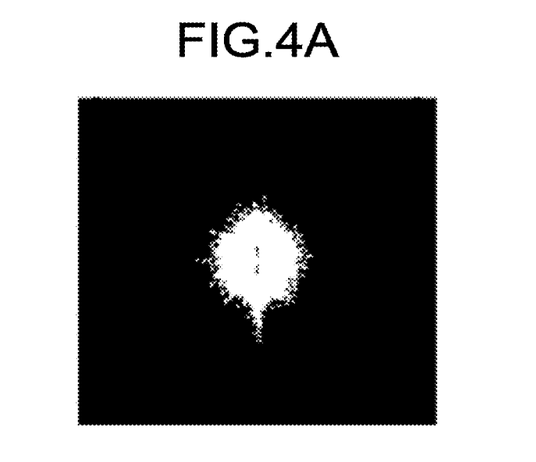
FIG. 4A is a view illustrating a simulation result.
Figure 4B:
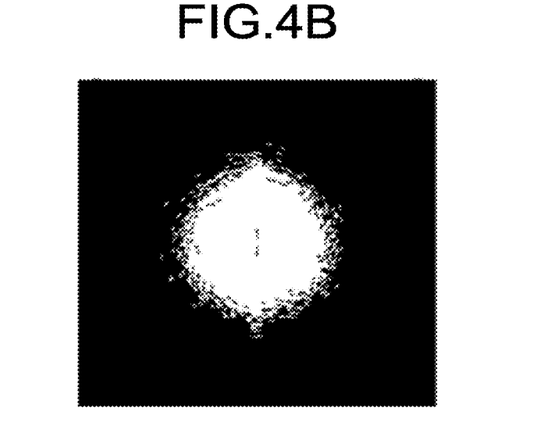
FIG. 4B is a view illustrating a simulation result.
Figure 4C:
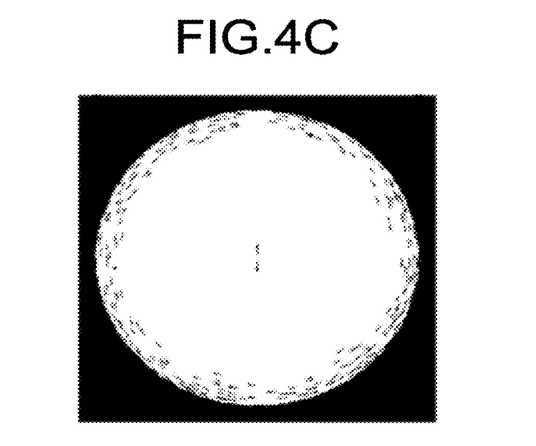
FIG. 4C is a view illustrating a simulation result.

FIGS. 4A, 4B, and 4C are views illustrating simulation results. FIGS. 4A, 4B, and 4C illustrate the cases where the distance D is 0 mm, 0.05 mm, and 0.125 mm, respectively. White portions indicate regions where the light intensity is high. When the distance D is 0 mm, a region with high light intensity is narrow, having a substantially Gaussian shape. That is, it is confirmed that, when the distance D is 0 mm, the skew ray component is not sufficiently generated in the optical fiber 2 having a length of 1 m, leading to insufficient execution of the beam profile conversion. In contrast, when the distance D is 0.05 mm, the profile has a top hat shape having a wider high light intensity region, and when the distance D is 0.125 mm, the profile has a top hat shape having a still wider high light intensity region. From this, it is confirmed that the beam profile conversion can be more efficiently performed by the optical fiber 2 having a length of 1 m by making the distance D larger than 0.

Other embodiments of the beam profile converter will be described below. The beam profile converters according to the following embodiments can individually be used in place of the beam profile converter 10 in the laser ablation device 1000 and the catheter device 100.

Furthermore, the beam profile converters according to the following embodiments may individually be provided as necessary with a housing a ferrule, a fiber fixing member, a resin, a light receiving element, an electric wire, or the like, similar to those for the beam profile converter 10.

Second Embodiment

Figure 5A:
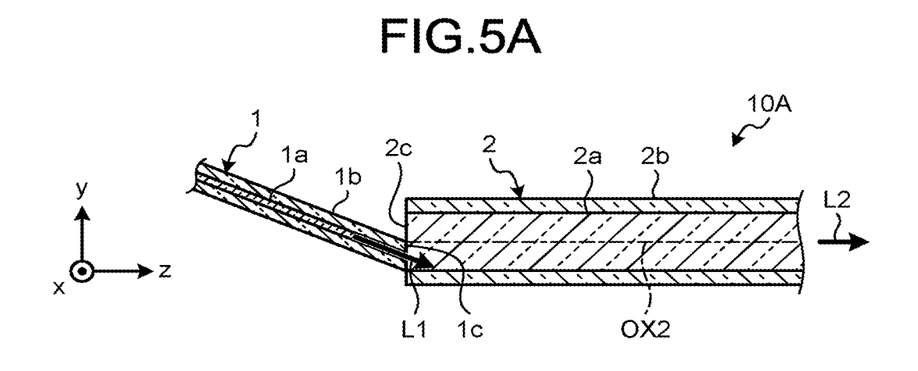
FIG. 5A is a schematic diagram illustrating a schematic configuration of main portions of a beam profile converter according to a second embodiment.
Figure 5B:
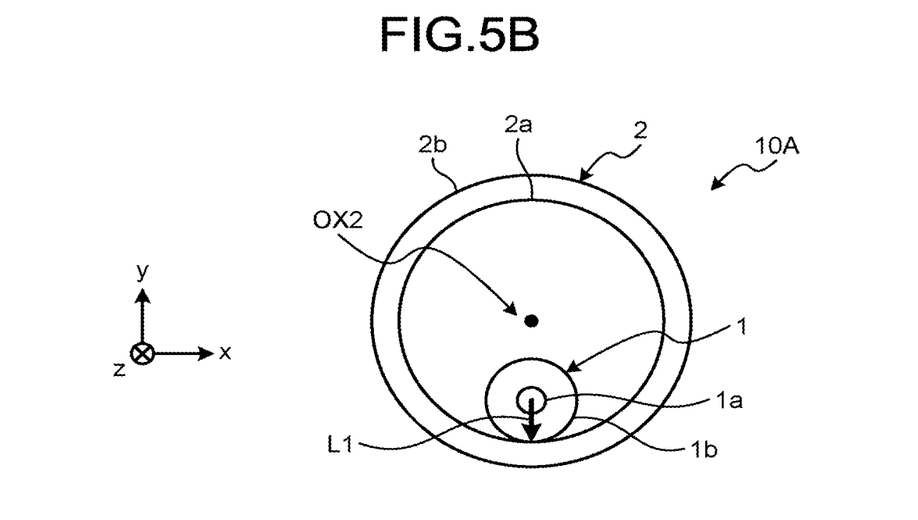
FIG. 5B is a schematic diagram illustrating an output/input state of laser light of the beam profile converter according to the second embodiment.

FIG. 5A is a schematic diagram illustrating a schematic configuration of main portions of a beam profile converter according to a second embodiment. FIG. 5B is a schematic view illustrating an input/output state of laser light, an illustration of the optical fibers 1 and 2 of FIG. 5A viewed in the negative direction of the z axis.

In this beam profile converter 10A, the end surface 1c of the obliquely cut optical fiber 1 and the end surface 2c of the optical fiber 2 are fusion-spliced. At this time, an optical axis (not illustrated) of the optical fiber 1 and the optical axis OX2 of the optical fiber 2 are separated in the y direction on a fusion-spliced surface. With this arrangement, the end surface 1c and the end surface 2c are parallel to each other, while the optical axis of the optical fiber 1 and the optical axis OX2 of the optical fiber 2 are inclined to each other within a plane parallel to the yz plane.

With the above configuration, the beam profile converter 10A achieves an input state in which the laser light L1 is input in a direction inclined with respect to the end surface 2c at a position separated from the optical axis OX2. Therefore, similarly to the beam profile converter 10, the beam profile converter 10A has advantageous effects of a simple configuration, low cost, and efficiency.

Here, when optical fibers having mutually different outer diameters are fused to each other, reflected return light is incident on the cladding of the optical fiber on the input side, which causes the resin or the like to generate heat. Therefore, in order to suppress the heat generation of the resin or the like, it is desirable to provide a heat dissipating portion on the fusion-spliced side of the coating portion of the input-side optical fiber. The heat dissipating porting is formed by applying heat dissipation silicone, for example.

Third Embodiment

Figure 6A:
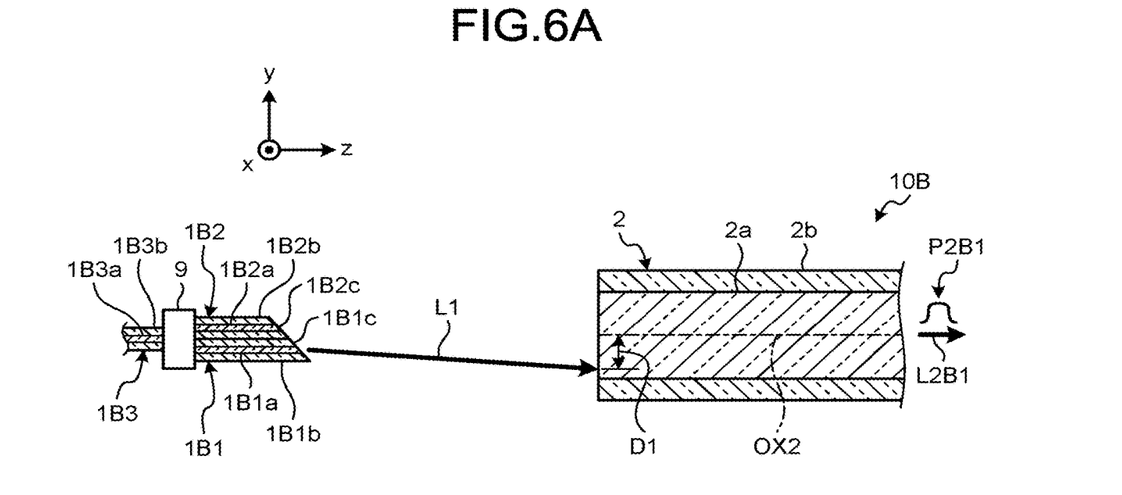
FIG. 6A is a schematic diagram illustrating a schematic configuration of main portions of a beam profile converter according to a third embodiment.
Figure 6B:
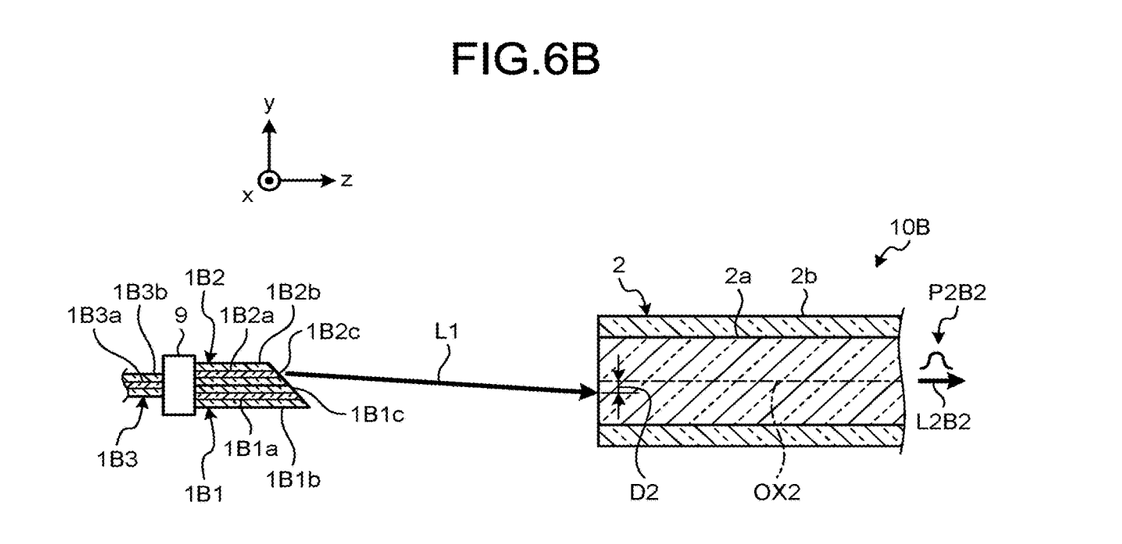
FIG. 6B is a schematic diagram illustrating a schematic configuration of main portions of the beam profile converter according to the third embodiment.

FIGS. 6A and 6B are schematic diagrams each illustrating a schematic configuration of main portions of the beam profile converter according to a third embodiment. A beam profile converter 10B includes optical fibers 1B1, 1B2, 1B3, a selector 9, and an optical fiber 2.

The optical fiber 1B3 includes a core portion 1B3a and a cladding portion 1B3b having configurations similar to the corresponding components in the optical fiber 1, and is optically connected to the connecting portion 1003. The optical fiber 1B3 guides the laser light L1 input from the connecting portion 1003 so as to be output to the selector 9.

The selector 9 selectively outputs the input laser light L1 to either the optical fibers 1B1 or 1B2. That is, the selector 9 has a function of selectively outputting the laser light L1 from either of the optical fibers 1B1 or 1B2. The selector 9 includes an optical switch, for example, receives an input of a control signal from a controller (not illustrated) or the like and switches output destinations of the laser light L1.

The optical fiber 1B1 as the first optical fiber includes a core portion 1B1a and a cladding portion 1B1b having a configuration similar to the corresponding configuration in the optical fiber 1. Furthermore, the optical fiber 1B1 has an end surface 1B1c that is obliquely cut, as the first end surface. The optical fiber 1B2 as the first optical fiber includes a core portion 1B2a and a cladding portion 1B2b having a configuration similar to the corresponding configuration in the optical fiber 1. Furthermore, the optical fiber 1B2 has an end surface 1B2c that is obliquely cut, as the first end surface. The optical axes of the optical fibers 1B1 and 1B2 extend in the z direction at positions different from each other in the y direction.

Here is a case, as illustrated in FIG. 6A, where the laser light L1 is output from the optical fiber 1B1. When the laser light L1 is input to the core portion 2a on the end surface 2c, the light L1 is input in a direction inclined with respect to the end surface 2c at a position separated from the optical axis OX2 of the optical fiber 2 by a distance D1. As a result, the optical fiber 2 performs beam profile conversion and outputs laser light L2B1 having a beam profile P2B1 having a predetermined top hat shape.

Here is another case, as illustrated in FIG. 6B, where the laser light L1 is output from the optical fiber 1B2. When the laser light L1 is input to the core portion 2a on the end surface 2c, the laser light L1 is input in a direction inclined with respect to the end surface 2c at a position separated from the optical axis OX2 of the optical fiber 2 by a distance D2 shorter than the distance D1. As a result, the optical fiber 2 performs beam profile conversion and outputs laser light L2B2 having a beam profile P2B2 having a top hat shape, different from the beam profile P2B1.

That is, beams of the laser light L1 individually output from the end surfaces 1B1c and 1B2c are input to the core portion 2a at positions where the distances from the optical axis OX2 of the optical fiber 2 are different from each other.

In this manner, the beam profile converter 10B makes it possible to switch whether the laser light L1 is output from the optical fiber 1B1 or the optical fiber 1B2. With this configuration, similarly to the beam profile converter 10, the beam profile converter 10B achieves a simple configuration, low cost, and high efficiency, as well as outputting switched beams of laser light having mutually different top hat-shaped beam profiles.

In the beam profile converter 10B, the following selector may be adopted instead of the selector 9. That is, an input-side optical connector is provided individually at the end of the optical fiber 1B1 opposite to the end surface 1B1c and the end of the optical fiber 1B2 opposite to the end surface 1B2c. Together with this, an output-side optical connector is provided at the connecting portion 1003. With this configuration, it is allowable to employ a selector in which either the output-side optical connector or the input-side optical connector is connectable. The beam profile converter 10B includes two optical fibers 1B1 and 1B2 as a plurality of the first optical fibers, but may have a configuration including three or more first optical fibers. In this case, the three or more first optical fibers can be formed by using an optical fiber bundle, for example.

Fourth Embodiment

Figure 7:
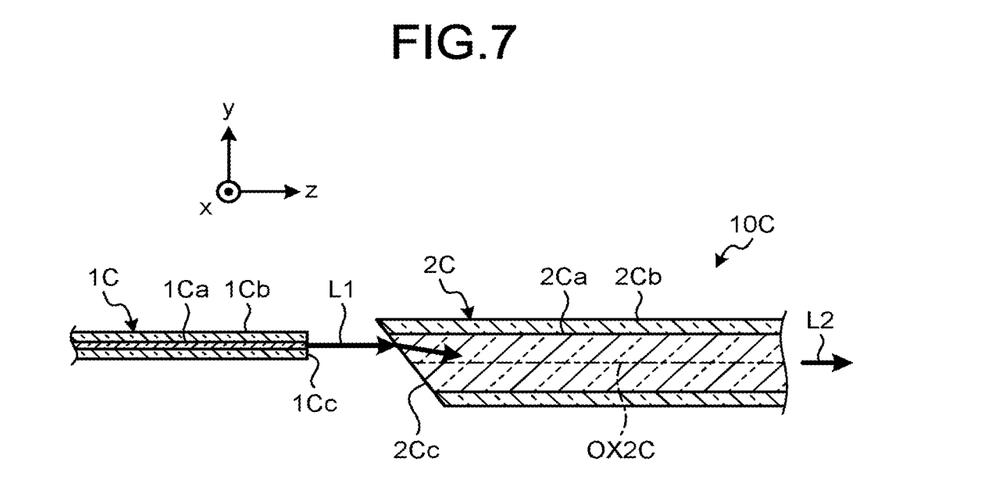
FIG. 7 is a schematic diagram illustrating a schematic configuration of main portions of a beam profile converter according to a fourth embodiment.

FIG. 7 is a schematic diagram illustrating a schematic configuration of main portions of a beam profile converter according to a fourth embodiment. The beam profile converter 10C includes an optical fiber 1C and an optical fiber 2C.

The optical fiber 1C, which is the first optical fiber, includes a core portion 1Ca and a cladding portion 1Cb each having a configuration similar to the corresponding component in the optical fiber 1. The optical fiber 1C has an end surface 1Cc as a first end surface. The end surface 1Cc is orthogonal to an optical axis (not illustrated) of the optical fiber 1C extending in the z direction and is parallel to the xy plane.

The optical fiber 2C, which is the second optical fiber, includes a core portion 2Ca and a cladding portion 2Cb each having a configuration similar to the corresponding component in the optical fiber 2. The optical fiber 2C has an end surface 2Cc as a second end surface. The end surface 2Cc is parallel to the x axis and is inclined with respect to an optical axis OX2C of the optical fiber 2C extending in the z direction. That is, the optical fiber 2C is cut obliquely. Furthermore, the end surface 1Cc and the end surface 2Cc are non-parallel to each other. The optical axis of the optical fiber 1C and the optical axis OX2C of the optical fiber 2C are parallel to each other, but are separated from each other in the y direction.

In the beam profile converter 10C, the optical fiber 1C outputs the guided laser light L1 from the end surface 1Cc. The laser light L1 output from the end surface 1Cc travels in the z direction.

Since the core diameter of the optical fiber 2C is larger than the core diameter of the optical fiber 1C, the laser light L1 output from the end surface 1Cc is input to the core portion 2Ca of the end surface 2Cc at a position separated from the optical axis OX2C. Here, the end surface 2Cc is inclined with respect to the z axis. As a result, due to a refractive index difference between the core portion 2Ca and the space inside the housing 3, the laser light L1 input from the end surface 2Cc is to be input, in the end surface 2Cc, in a direction inclined from the optical axis OX2C within a plane parallel to the yz plane. That is, the laser light L1 output from the optical fiber 1C is parallel to the optical axis OX2C of the optical fiber 2C until immediately before being input to the core portion 2Ca but is to be refracted in a direction inclined with respect to the optical axis OX2C of the optical fiber 2C after being input to the core portion 2Ca on the end surface 2Cc at a position separated from the optical axis OX2C of the optical fiber 2C. With this configuration, in the beam profile converter 10C, the optical fiber 2C functions as an optical fiber that converts the beam profile and outputs the laser light L2, similarly to the case of the beam profile converter 10. As a result, the beam profile converter 10C can efficiently perform beam profile conversion at low cost with a simple configuration.

Note that it is sufficient as long as the input state in which the laser light L1 is input in the direction inclined with respect to the end surface 2Cc can be achieved at a position separated from the optical axis OX2C. Therefore, the configuration of the beam profile converter 10C may be modified so that the optical axis of the optical fiber 1C and the optical axis OX2C become non-parallel to each other.

Furthermore, it is possible to adjust the beam profile of the laser light L2 by appropriately adjusting the inclination angle of the end surface 2Cc with respect to the optical axis OX2C, the distance between the end surface 1Cc and the end surface 2Cc, and a combination of the core diameter and refractive index of the core portion 1Ca, and the core diameter and the refractive index of the core portion 2Ca.

Fifth Embodiment

Figure 8:
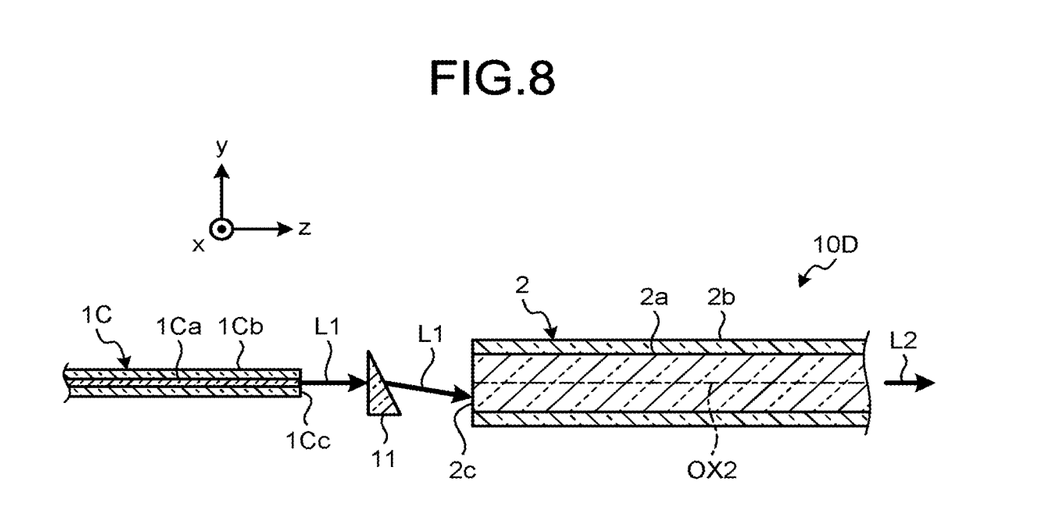
FIG. 8 is a schematic diagram illustrating a schematic configuration of main portions of a beam profile converter according to a fifth embodiment.

FIG. 8 is a schematic diagram illustrating a schematic configuration of main portions of a beam profile converter according to a fifth embodiment. A beam profile converter 10D has a configuration including an optical fiber 1C and an optical fiber 2, in which a triangular prism 11 is disposed between an end surface 1Cc of the optical fiber 1C and an end surface 2c of the optical fiber 2.

In the beam profile converter 10D, the optical fiber 1C outputs the guided laser light L1 from the end surface 1Cc. The laser light L1 output from the end surface 1Cc travels in the z direction and is input to the triangular prism 11. The triangular prism 11 is an example of an optical element that refracts the laser light L1. The triangular prism 11 refracts the laser light L1 so that the traveling direction of the laser light L1 becomes a direction inclined from the z axis within a plane parallel to the yz plane. As a result, the laser light L1 is input to the core portion 2a of the end surface 2c of the optical fiber 2 at a position separated from the optical axis OX2, input, at the end surface 2c, in a direction inclined from the optical axis OX2 within a plane parallel to the yz plane. With this configuration, the optical fiber 2 outputs the laser light L2 having a converted beam profile. As a result, the beam profile converter 10D can efficiently perform beam profile conversion at low cost with a simple configuration, similarly to the case of the beam profile converter 10.

The triangular prism 11 may be provided in contact with the end surface 2c of the optical fiber 2. In this case, the laser light L1 output from the end surface 1Cc of the optical fiber 1C is parallel to the optical axis OX2 of the optical fiber 2 until immediately before being input to the triangular prism 11. However, the laser light L1 is refracted by the triangular prism 11 so as to become inclined with respect to the optical axis OX2 when being input to the core portion 2a on the end surface 2c. Furthermore, the triangular prism 11 may be provided in contact with the end surface 1Cc of the optical fiber 1C. Even in this case, the laser light L1 is input in the direction inclined from the optical axis OX2 immediately after being input to the core portion 2a of the end surface 2c.

Sixth Embodiment

Figure 9:
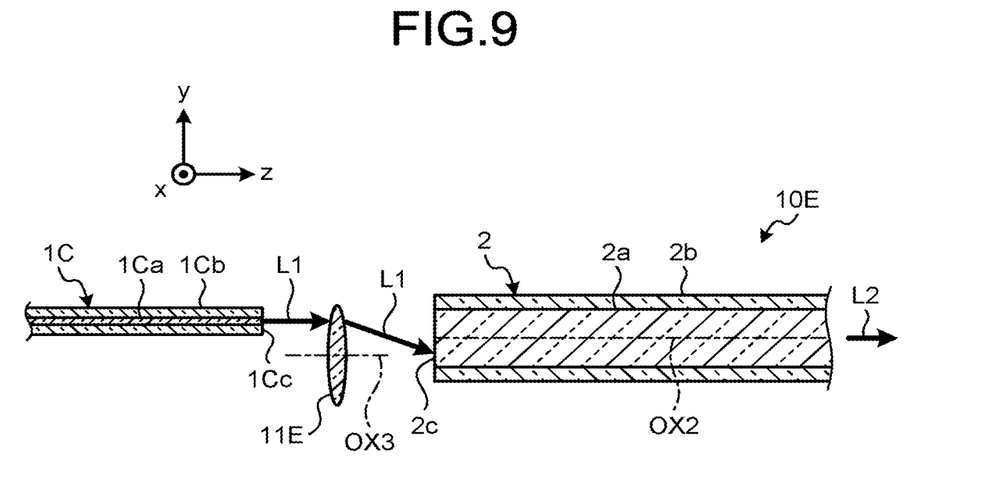
FIG. 9 is a schematic diagram illustrating a schematic configuration of main portions of a beam profile converter according to a sixth embodiment.

FIG. 9 is a schematic diagram illustrating a schematic configuration of main portions of a beam profile converter according to a sixth embodiment. A beam profile converter 10E has a configuration in which the triangular prism 11 has been replaced with a lens 11E which is an example of an optical element that refracts the laser light L1 in the configuration of the beam profile converter 10D illustrated in FIG. 8.

The lens 11E is arranged between the end surface 1Cc and the end surface 2c so that an optical axis OX3 would not be aligned with either the optical axis of the optical fiber 1C or the optical axis OX2 of the optical fiber 2. With this configuration, similarly to the case of the beam profile converter 10D, the laser light L1 output from the end surface 1Cc is refracted by the lens 11E so that the traveling direction of the laser light L1 becomes a direction inclined from the z axis within a plane parallel to the yz plane. As a result, the laser light L1 is input to the core portion 2a of the end surface 2c of the optical fiber 2 at a position separated from the optical axis OX2, input, at the end surface 2c, in a direction inclined from the optical axis OX2 within a plane parallel to the yz plane. With this configuration, the optical fiber 2 outputs the laser light L2 having a converted beam profile. As a result, the beam profile converter 10E can efficiently perform beam profile conversion at low cost with a simple configuration, similarly to the case of the beam profile converter 10.

The lens 11E may be provided in contact with the end surface 2c of the optical fiber 2. In this case, the laser light L1 output from the end surface 1Cc of the optical fiber 1C is parallel to the optical axis OX2 of the optical fiber 2 until immediately before being input to the lens 11E. However, the laser light L1 is refracted by the lens 11E so as to become inclined with respect to the optical axis OX2 when being input to the core portion 2a on the end surface 2c. Furthermore, the lens 11E may be provided in contact with the end surface 1Cc of the optical fiber 1C. Even in this case, the laser light L1 is input in the direction inclined from the optical axis OX2 at a point where being input to the core portion 2a of the end surface 2c.

Seventh and Eighth Embodiments

As illustrated in FIGS. 2 and 3, after being output from the optical fiber 1, the laser light L1 in the beam profile converter 10 travels within a plane parallel to the yz plane and including the optical axes OX1 and OX2, so as to be input to the optical fiber 2. However, the input/output state of the laser light L1 is not limited to this example. For example, in a beam profile converter 10F according to a seventh embodiment illustrated in FIG. 10A, the optical axis of the optical fiber 1 and the optical axis OX2 of the optical fiber 2 are separated from each other to form a plane parallel to the zx plane. After being output from the optical fiber 1, the laser light L1 travels in a direction parallel to the yz plane and inclined with respect to the z axis, so as to be input to the optical fiber 2. In this case, the traveling direction of the laser light L1 and the optical axis OX2 have a twisted positional relationship. At this time, the optical fiber 1 is arranged so that the end surface 1c is parallel to the xy plane.

Figure 10A:
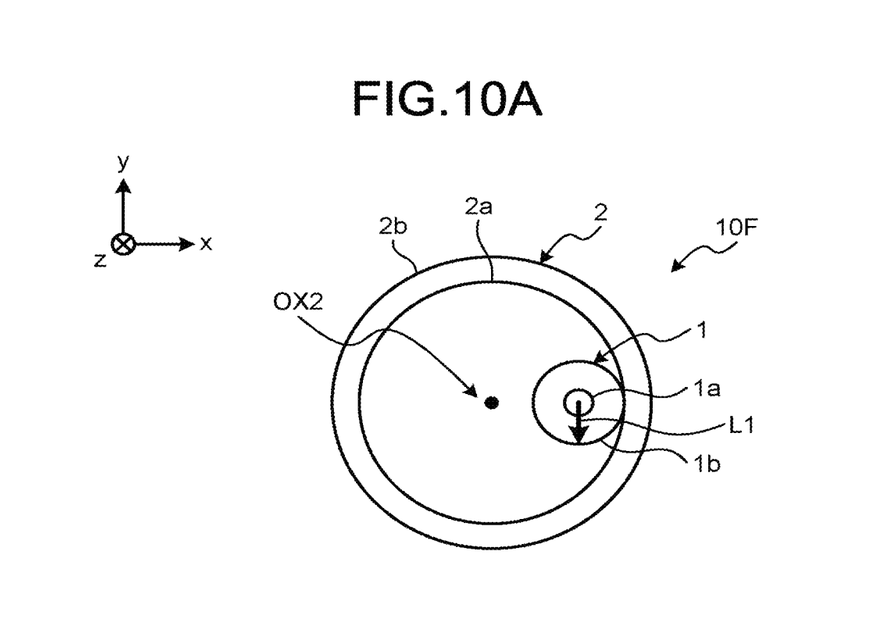
FIG. 10A is a view illustrating a laser light input/output state in a beam profile converter according to a seventh embodiment.
Figure 10B:
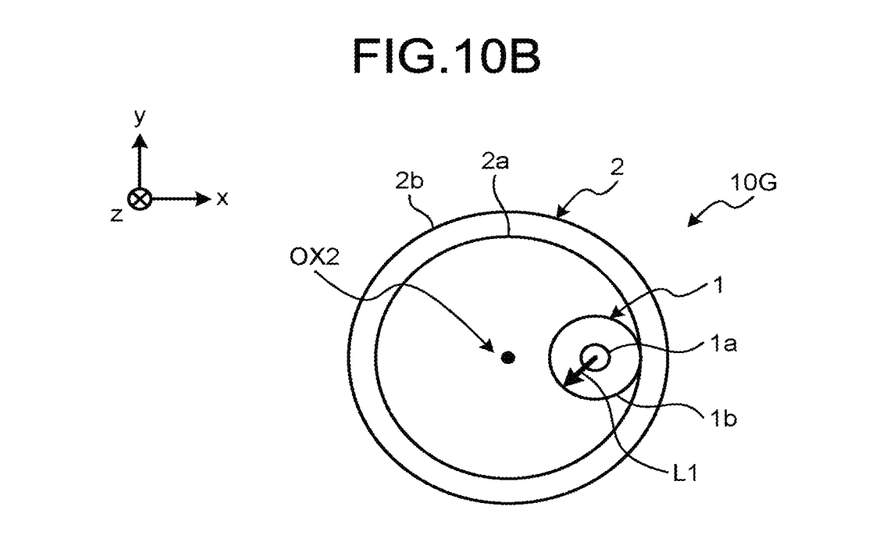
FIG. 10B is a view illustrating an input/output state of laser light in a beam profile converter according to an eighth embodiment.

Moreover, in a beam profile converter 10G according to an eighth embodiment illustrated in FIG. 10B, the optical axis of the optical fiber 1 and the optical axis OX2 of the optical fiber 2 are separated from each other to form a plane parallel to the zx plane. After being output from the optical fiber 1, the laser light L1 travels in a direction inclined with respect to any of the xy plane, the yz plane, and the zx plane, so as to be input to the optical fiber 2. Even in this case, the traveling direction of the laser light L1 and the optical axis OX2 have a twisted positional relationship. At this time, the optical fiber 1 is arranged in a state of being rotated about the optical axis by about 45° clockwise from the state of the optical fiber 1 in FIG. 10A. That is, as illustrated in FIGS. 10A and 10B, the traveling direction of the laser light L1 and the optical axis OX2 may have a twisted positional relationship. In addition, it is allowable also in other embodiments to have a twisted positional relationship between the optical axis of the second optical fiber and the traveling direction of the laser light input to the second optical fiber.

Ninth Embodiment

Figure 11:
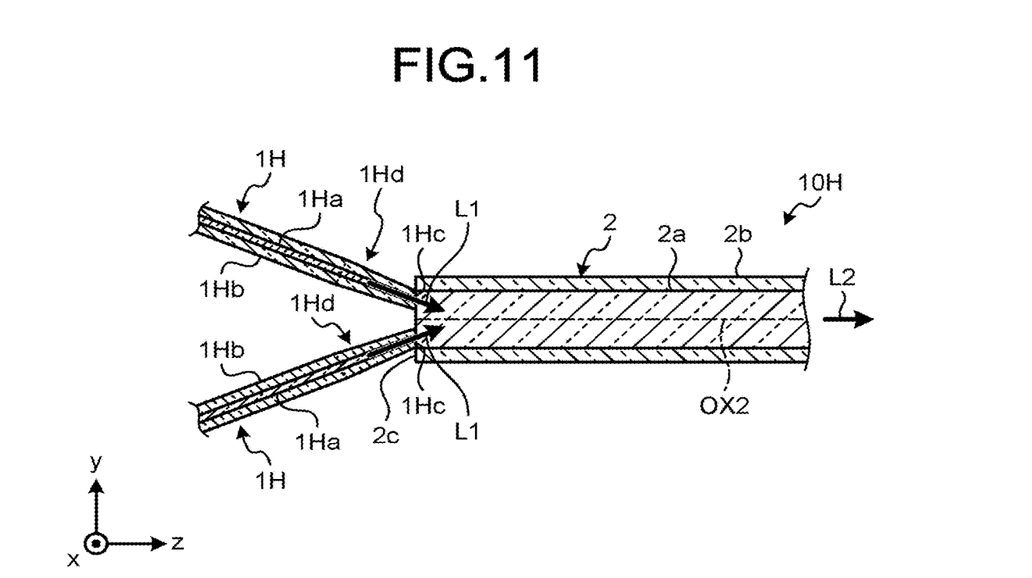
FIG. 11 is a schematic diagram illustrating a schematic configuration of main portions of a beam profile converter according to a ninth embodiment.

FIG. 11 is a schematic diagram illustrating a schematic configuration of main portions of the beam profile converter according to a ninth embodiment. A beam profile converter 10H includes two optical fibers 1H and an optical fiber 2.

Each of the two optical fibers 1H includes a core portion 1Ha and a cladding portion 1Hb each having a configuration similar to the corresponding component in the optical fiber 1. Furthermore, each of the optical fibers 1H has an end surface 1Hc that is oblique to each of optical axes. Furthermore, each of the optical fibers 1H has a tapered portion 1Hd in which the core portion 1Ha and the cladding portion 1Hb are tapered in diameter toward the end surface 1Hc side.

In this beam profile converter 10H, the end surface 1Hc of each of the optical fibers 1H that is inclined with respect to the optical axis is fusion-spliced with the end surface 2c of the optical fiber 2. At this time, the optical axis of each of the optical fibers 1H and the optical axis OX2 of the optical fiber 2 are separated from each other in the y direction on the fusion-spliced surface. With this arrangement, the end surface 1Hc and the end surface 2c are parallel to each other, while the optical axis of each of the optical fibers 1H and the optical axis OX2 of the optical fiber 2 are inclined to each other within a plane parallel to the yz plane. The core diameter of the optical fiber 2 is larger than the core diameter of the end surface 1Hc of each of the optical fibers 1H. Here, the core diameter at the end surface 1Hc is a core diameter at a tip end surface where the core portion 1Ha has a tapered diameter. The core diameter of the non-tapered portion of each of the optical fibers 1H may be larger than the core diameter of the optical fiber 2.

With the above configuration, the beam profile converter 10H realizes an input state in which the laser light L1 output from each of the optical fibers 1H is input in a direction inclined with respect to the end surface 2c at a position separated from the optical axis OX2. Therefore, similarly to the beam profile converter 10, the beam profile converter 10A has advantageous effects of a simple configuration, low cost, and efficiency. Furthermore, in the optical fiber 1H, since the core portion 1Ha is tapered in diameter in the tapered portion 1Hd, the laser light L1 having higher luminance than in the case where no tapering is performed is output from the core portion 1Ha in the end surface 1Hc. As a result, the output laser light L2 having the beam profile converted by the optical fiber 2 also has higher luminance. Furthermore, the laser light L2 is a combination of the two beams of the laser light L1, and thus, has high intensity.

Tenth Embodiment

Figure 12:
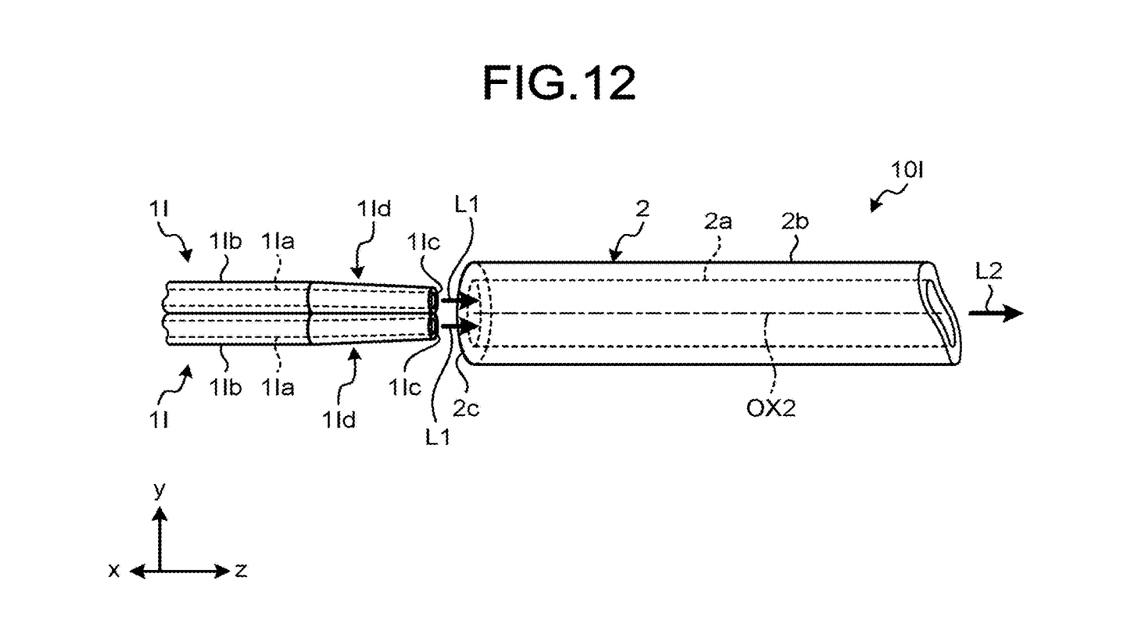
FIG. 12 is a schematic diagram illustrating a schematic configuration of main portions of a beam profile converter according to a tenth embodiment.

FIG. 12 is a schematic diagram illustrating a schematic configuration of main portions of a beam profile converter according to a tenth embodiment. The beam profile converter 10I includes two optical fibers 1I and an optical fiber 2.

Each of the two optical fibers 1I includes a core portion 1Ia and a cladding portion 1Ib each having a configuration similar to the corresponding component in the optical fiber 1. Furthermore, each of the optical fibers 1I has an end surface 1Ic. Furthermore, each of the optical fibers 1I has a tapered portion 1Id in which the core portion 1Ia and the cladding portion 1Ib are tapered in diameter toward the end surface 1Ic side. While the end surfaces 1Ic of the two optical fibers 1I and the end surface 2c of the optical fiber 2 are fusion-spliced, the optical fibers 1I and 2 are separated in FIG. 12 for illustrative purposes.

The two optical fibers 1I are formed by bundling two optical fibers like the optical fiber 1C illustrated in FIG. 7 that are not obliquely cut and have a constant core diameter and cladding diameter in the longitudinal direction, having ends of the bundled fibers heated and squeezed to form the tapered portions 1Id. Therefore, the two tapered portions 1Id have an obliquely truncated cone shape. Specifically, when viewed in the positive direction of the x axis, the two tapered portions 1Id have trapezoidal shapes with the end surface 1Ic as an upper base and the base end side of the tapered portion 1Id as a lower base. Both the upper and lower bases are parallel to the xy plane. Furthermore, of the outer peripheral surfaces of the two tapered portions 1Id, the facing sides are in line contact with each other so as to extend in the z direction while the non-facing sides are inclined with respect to the z axis. Accordingly, the optical axis in the tapered portion 1Id of each of the two optical fibers 1I is inclined with respect to the z axis.

The end surface 1Ic of the two optical fibers 1I and the end surface 2c of the optical fiber 2 are fusion-spliced in a state where the optical axis in the tapered portion 1Id and the optical axis OX2 are separated in the y-axis direction. As a result, beams of the laser light L1 output from the two optical fibers 1I are input to the core portion 2a of the end surface 2c of the optical fiber 2 at a position separated from the optical axis OX2 and are input in a direction inclined from the optical axis OX2 within the yz plane on the end surface 2c. With this configuration, the optical fiber 2 outputs the laser light L2 having a converted beam profile. As a result, the beam profile converter 10I can efficiently perform beam profile conversion at low cost with a simple configuration, similarly to the case of the beam profile converter 10. Furthermore, similarly to the case of the beam profile converter 10H illustrated in FIG. 11, the laser light L2 that is output after beam profile conversion in the optical fiber 2 is a combination of the two beams of the laser light L1 and thus has high luminance and intensity. Note that similarly to the case of the ninth embodiment, while the core diameter of the optical fiber 2 is larger than the core diameter of the end surface 1Ic of each of the optical fibers 1I, the core diameter of the non-tapered portion of each of the optical fibers 1I need not be larger than the core diameter of the optical fiber 2.

Eleventh Embodiment

Figure 13A:
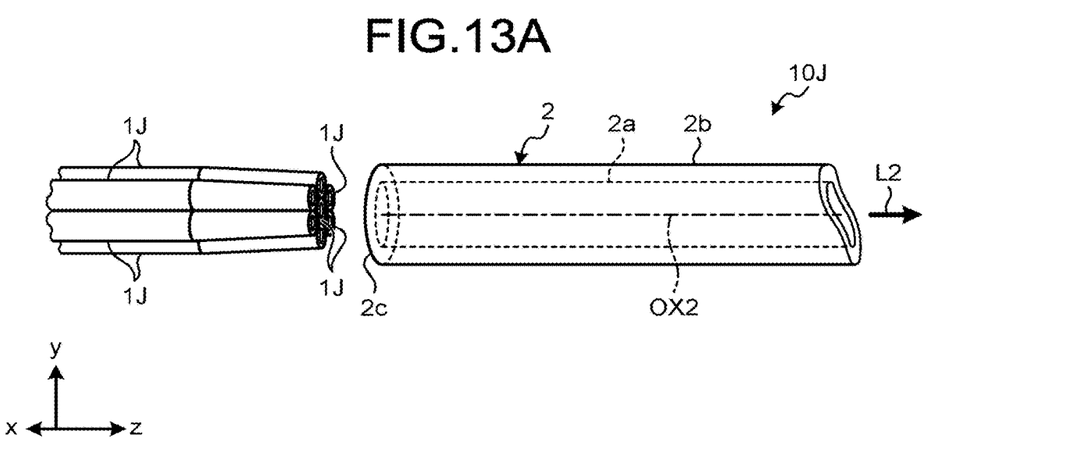
FIG. 13A is a schematic diagram illustrating a schematic configuration of main portions of a beam profile converter according to an eleventh embodiment.

FIG. 13A is a schematic diagram illustrating a schematic configuration of main portions of a beam profile converter according to an eleventh embodiment. The beam profile converter 10J includes seven optical fibers 1J and an optical fiber 2.

Figure 13B:
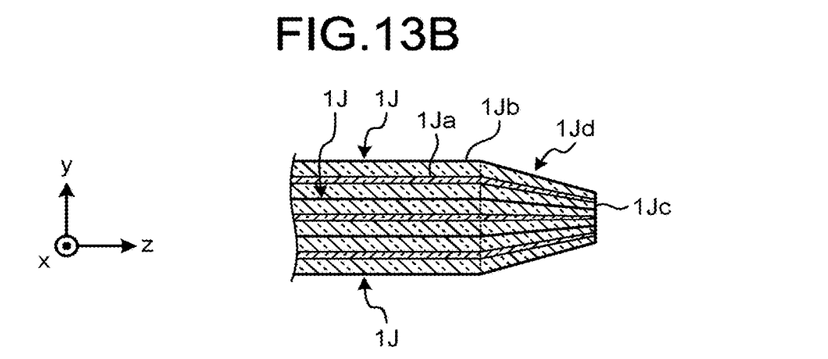
FIG. 13B is a schematic diagram illustrating a cross section of the beam profile converter according to the eleventh embodiment.

The seven optical fibers 1J form an optical fiber bundle in which six optical fibers 1J are arranged on the outer circumference of the central optical fiber 1J. FIG. 13B is a view illustrating a cross section of the optical fiber bundle cut along a plane that includes the optical axis of the central optical fiber 1J and is parallel to the yz plane. Each of the seven optical fibers 1J includes a core portion 1Ja and a cladding portion 1Jb having a configuration similar to the corresponding components in the optical fiber 1. Furthermore, each of the optical fibers 1J has an end surface 1Jc. Furthermore, each of the optical fibers 1J has a tapered portion 1Jd in which the core portion 1Ja and the cladding portion 1Jb are tapered in diameter toward the end surface 1Jc side. While the end surfaces 1Jc of the seven optical fibers 1J and the end surface 2c of the optical fiber 2 are fusion-spliced, the optical fibers 1J and the optical fiber 2 are separated in FIG. 13A for illustrative purposes.

The seven optical fibers 1J are formed by bundling seven optical fibers that are not obliquely cut and have a constant core diameter and cladding diameter in the longitudinal direction, having ends of the optical fiber bundle heated and squeezed to form the tapered portions 1Jd. Therefore, of the seven tapered portions 1Jd, the one located at the center has a truncated cone shape while the others located at the outer periphery each have an obliquely truncated cone shape. Therefore, the optical axes of the tapered portions 1Jd of the six optical fibers 1J located on the outer circumference are inclined with respect to the z axis.

Figure 13C:
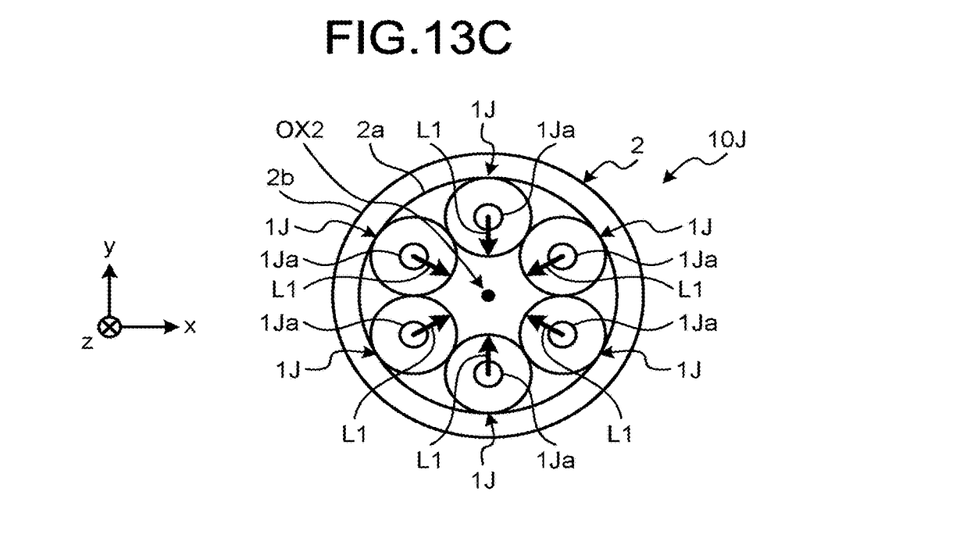
FIG. 13C is a schematic diagram illustrating an input/output state of laser light of the beam profile converter according to the eleventh embodiment.

The end surfaces 1Ic of the seven optical fibers 1J and the end surface 2c of the optical fiber 2 are fusion-spliced such that the optical axis of the centrally located optical fiber 1J and the optical axis OX2 are aligned with each other. As a result, the optical axes of the six tapered portions 1Id located on the outer periphery and the optical axis OX2 are fusion-spliced in a state of being separated in the y-axis direction. As a result, beams of the laser light L1 output from the six optical fibers 1J located on the outer periphery are input to the core portion 2a of the end surface 2c of the optical fiber 2 at a position separated from the optical axis OX2 and are input in a direction inclined from the optical axis OX2 within the yz plane at the end surface 2c. FIG. 13C is a schematic diagram illustrating an input/output state of laser light. Note that the optical fiber 1J located at the center is not illustrated.

With this configuration, the optical fiber 2 outputs the laser light L2 having a converted beam profile. As a result, the beam profile converter 10J can efficiently perform beam profile conversion at low cost with a simple configuration, similarly to the case of the beam profile converter 10. Furthermore, the laser light L2 that is output after beam profile conversion in the optical fiber 2 is a combination of the six beams of the laser light L1 and thus has high luminance and intensity. Furthermore, since the six beams of the laser light L1 are input to the optical axis OX2 of the optical fiber 2 substantially in axial symmetry, it is possible to obtain a more suitable beam profile with higher uniformity around the axis. Note that similarly to the case of the ninth embodiment, the core diameter of the optical fiber 2 is larger than the core diameter of the end surface 1Jc of each of the optical fibers 1J, the core diameter of the non-tapered portion of each of the optical fibers 1J need not be larger than the core diameter of the optical fiber 2.

In a case where the beam profile converter of the above-described embodiments is applied to a laser ablation device used to irradiate the epidermis of a patient with laser light, it would not be essential to use the catheter body 110 or the optical element 120.

Furthermore, the present disclosure is not limited to the above-described embodiments. The present disclosure also includes those obtained by appropriately combining the components of the above-described embodiments. Furthermore, further effects and modifications can be easily derived by those skilled in the art. Therefore, the broader aspects of the present disclosure and various modifications are conceivable, not limited to the above embodiments.

The beam profile converter, the catheter device, and the laser ablation device according to the present disclosure are useful for performing treatment by outputting laser light for ablation from the tip of an optical fiber to be applied to a target site such as an affected part.

REFERENCE SIGNS LIST

According to the present disclosure, it is possible to achieve an effect that the beam profile of laser light can be efficiently converted to a top hat shape with a simple configuration.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

The invention claimed is:

1. A beam profile converter comprising:
   a plurality of first optical fibers each of which outputs guided light from a first end surface respectively;
   a second optical fiber being a multi-mode optical fiber to which the light is input to a second end surface and configured to guide the light, wherein:
      a core diameter of the second optical fiber is larger than a core diameter of the first optical fiber on the first end surface, and
      the light output from the first end surface is input to a core portion of the second end surface at a position separated from an optical axis of the second optical fiber in a direction inclined with respect to the second end surface;
   a selector that selectively outputs the light from any of the plurality of first optical fibers, wherein the light output from the first end surface of each of the plurality of first optical fibers is input to the core portion of the second end surface at positions where separation distances from the optical axis of the second optical fiber are different from each other; and
   an optical element designed to refract the light, provided between the first end surface of the first optical fiber and the second end surface of the second optical fiber.

2. The beam profile converter according to claim 1, wherein
   the first end surface and the second end surface are non-parallel to each other.

3. The beam profile converter according to claim 1, wherein
   the first end surface of the first optical fiber and the second end surface of the second optical fiber are fusion-spliced to each other, and an optical axis of the first optical fiber and the optical axis of the second optical fiber are separated and inclined from each other on a fusion-spliced surface.

4. The beam profile converter according to claim 1, wherein
   the first end surface is inclined with respect to the optical axis of the first optical fiber, or the second end surface is inclined with respect to the optical axis of the second optical fiber.

5. The beam profile converter according to claim 1, wherein,
   using a cladding diameter $\Phi_1$ at the first end surface of the first optical fiber and a core diameter $\Phi_2$ at the second end surface of the second optical fiber, a distance D between an input position of the light output from the first end surface to the second optical fiber and the optical axis of the second optical fiber is expressed by Formula (1):
   $$(\Phi_2-\Phi_1)/2 > D \geq \Phi_1/2 \qquad (1).$$

6. The beam profile converter according to claim 1, wherein
   the core diameter of the second optical fiber is 1.5 times or more larger than the core diameter of the first optical fiber on the first end surface.

7. The beam profile converter according to claim 1, wherein
   a beam profile of the light guided and output by the second optical fiber has a top hat shape.

8. The beam profile converter according to claim 1, wherein
   the first optical fiber has a tapered portion in which a core diameter and a cladding diameter are reduced toward a side of the first end surface.

9. A catheter device comprising:
   the beam profile converter according to claim 1, and
   a catheter body into which at least a part of the beam profile converter is to be inserted.

10. A laser ablation device comprising:
    the beam profile converter according to claim 1; and
    a laser light source that outputs the light that is laser light for ablation to the first optical fiber.

* * * * *